United States Patent
Heismann et al.

(10) Patent No.: US 10,365,342 B2
(45) Date of Patent: *Jul. 30, 2019

(54) METHOD AND DEVICE FOR DETERMINING A CHANGE OVER TIME IN A BIOMARKER IN A REGION TO BE EXAMINED

(71) Applicant: Siemens Healthcare GmbH, Erlangen (DE)

(72) Inventors: Björn Heismann, Erlangen (DE); Arne Hengerer, Möhrendorf (DE); Sebastian Schmidt, Weisendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 233 days.

This patent is subject to a terminal disclaimer.

(21) Appl. No.: 15/467,427

(22) Filed: Mar. 23, 2017

(65) Prior Publication Data
US 2017/0192071 A1 Jul. 6, 2017

Related U.S. Application Data

(63) Continuation of application No. 13/894,623, filed on May 15, 2013, now Pat. No. 9,651,639.

(30) Foreign Application Priority Data

May 15, 2013 (DE) .......................... 10 2012 209 059

(51) Int. Cl.
*G01R 33/485* (2006.01)
*G01R 33/483* (2006.01)
(Continued)

(52) U.S. Cl.
CPC ............ *G01R 33/485* (2013.01); *A61B 5/055* (2013.01); *G01R 33/48* (2013.01); *G01R 33/483* (2013.01);
(Continued)

(58) Field of Classification Search
CPC .... G01R 33/485; G01R 33/483; G01R 33/48; G01R 33/4806; G01R 33/5616; A61B 5/055

See application file for complete search history.

(56) References Cited

U.S. PATENT DOCUMENTS 5,119,817 A 6/1992 Allen
7,645,613 B2 1/2010 Ivey et al.
(Continued)

OTHER PUBLICATIONS

Michael W. Weiner et al: "The Alzheimer's Disease Neuroimaging Initiative: A review of papers published since its inception", in: Alzeimer's & Dementia, vol. 8, Feb. 2012, S. S1-S68, ISSN 1552-5260; 2012.

*Primary Examiner* — Dixomara Vargas
(74) *Attorney, Agent, or Firm* — Harness, Dickey & Pierce, P.L.C.

(57) ABSTRACT

A method for determining a change over time in a biomarker in a region to be examined of a patient is provided. The change is determined from magnetic resonance data using a magnetic resonance measuring system with sequences and protocols for measuring the biomarkers by functional resting state connectivity by rsfMRI, perfusion values, magnetic resonance spectra of voxels, or morphometry of organs. A control unit has programs which evaluates the biomarker and a data memory which stores the results of the evaluation and additional data. During a first examination, a quantity result of the biomarkers is determined and stored in the data memory. During a follow-up examination, at least one previous item of the result and additional data from the first examination stored in the data memory are used for determining a quantitative change in the biomarker.

31 Claims, 3 Drawing Sheets

(51) Int. Cl.
*A61B 5/055* (2006.01)
*G01R 33/48* (2006.01)
*G01R 33/561* (2006.01)
*G01R 33/563* (2006.01)

(52) U.S. Cl.
CPC ..... *G01R 33/4806* (2013.01); *G01R 33/5616* (2013.01); *G01R 33/56366* (2013.01)

(56) References Cited

U.S. PATENT DOCUMENTS

| | | | |
|---|---|---|---|
| 7,907,769 B2 | 3/2011 | Sammak et al. | |
| 8,189,900 B2 | 5/2012 | Sammak et al. | |
| 8,239,136 B2 | 8/2012 | Liew et al. | |
| 8,557,745 B2 | 10/2013 | Blank et al. | |
| 8,894,975 B2 * | 11/2014 | Gore | A61B 5/055 424/9.3 |
| 8,896,678 B2 | 11/2014 | Hyde et al. | |
| 8,896,679 B2 | 11/2014 | Hyde et al. | |
| 8,908,941 B2 | 12/2014 | Hyde et al. | |
| 8,929,624 B2 | 1/2015 | Knoplioch et al. | |
| 8,965,062 B2 | 2/2015 | Hyde et al. | |
| 9,055,974 B2 | 6/2015 | Goetz | |
| 9,069,996 B2 | 6/2015 | Hyde et al. | |
| 9,081,992 B2 | 7/2015 | Hyde et al. | |
| 9,092,691 B1 | 7/2015 | Beaumont et al. | |
| 9,651,639 B2 * | 5/2017 | Heismann | G01R 33/483 |
| 2005/0215884 A1 | 9/2005 | Greicius et al. | |
| 2006/0117397 A1 * | 6/2006 | Rutkowski | A01K 67/0275 800/12 |
| 2006/0246495 A1 * | 11/2006 | Garrett | C12Q 1/6883 435/6.18 |
| 2009/0104605 A1 * | 4/2009 | Siuzdak | C12Q 1/6883 435/6.18 |
| 2011/0105350 A1 * | 5/2011 | Garrett | C12Q 1/6883 506/9 |
| 2012/0201832 A1 * | 8/2012 | Eckhardt | C12N 15/113 424/158.1 |
| 2012/0238028 A1 * | 9/2012 | Reszka | G01N 33/564 436/71 |
| 2012/0286157 A1 * | 11/2012 | Fuhrmann | G01N 33/92 250/282 |
| 2015/0160238 A1 * | 6/2015 | Reszka | G01N 33/6893 506/12 |

* cited by examiner

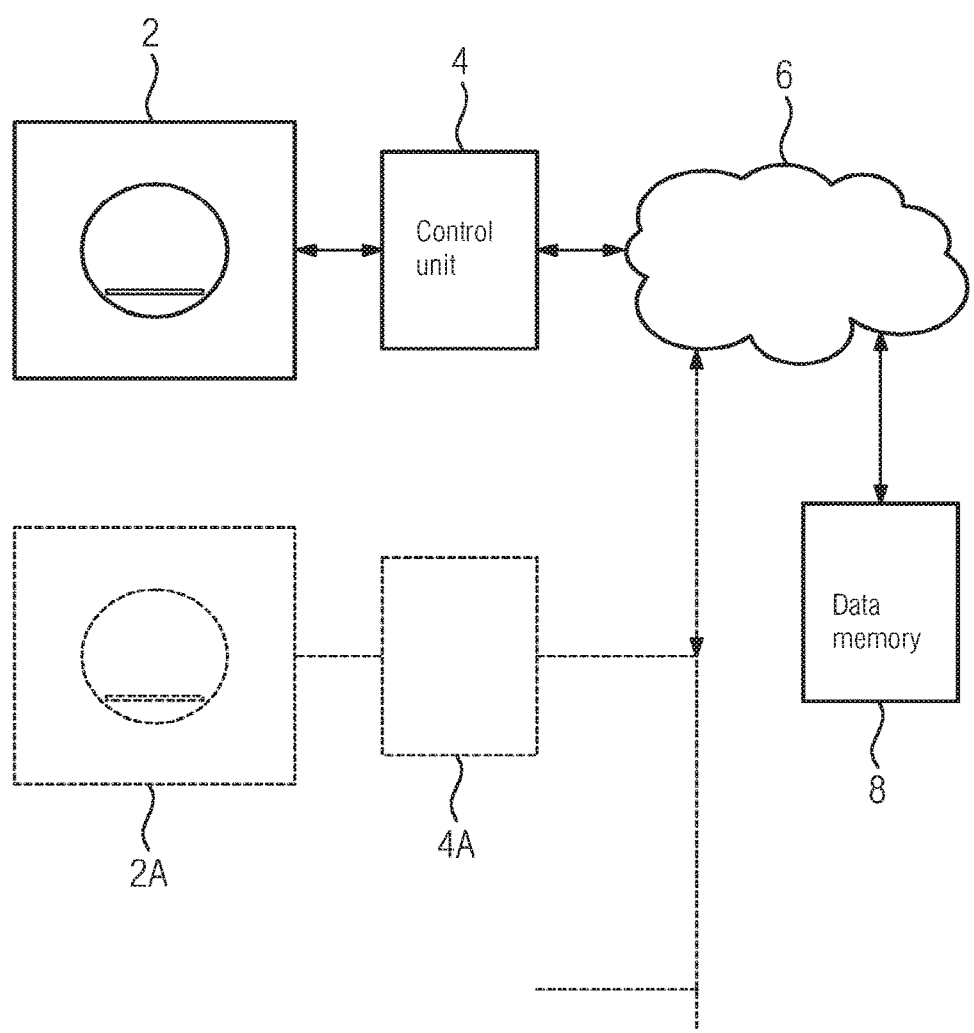

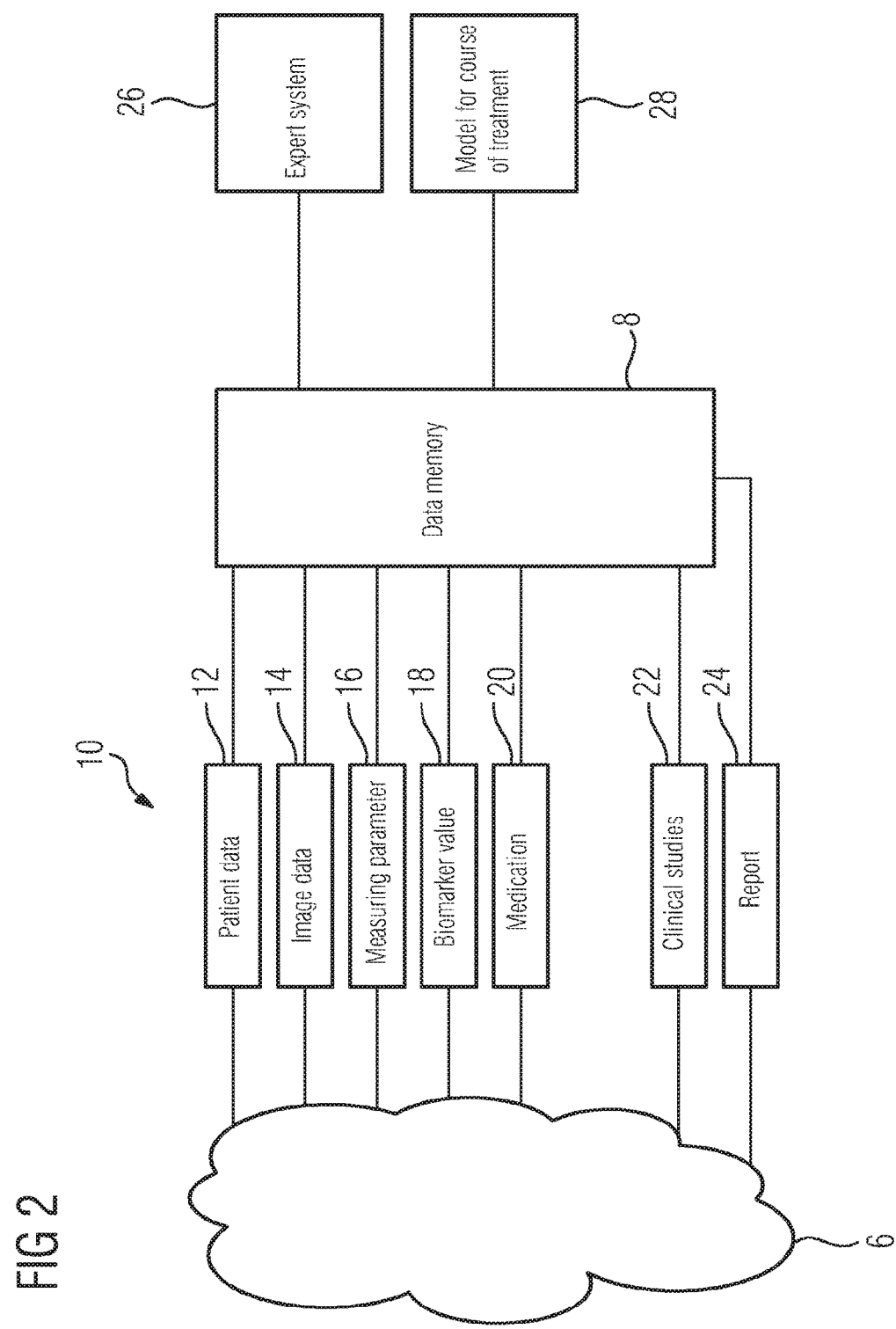

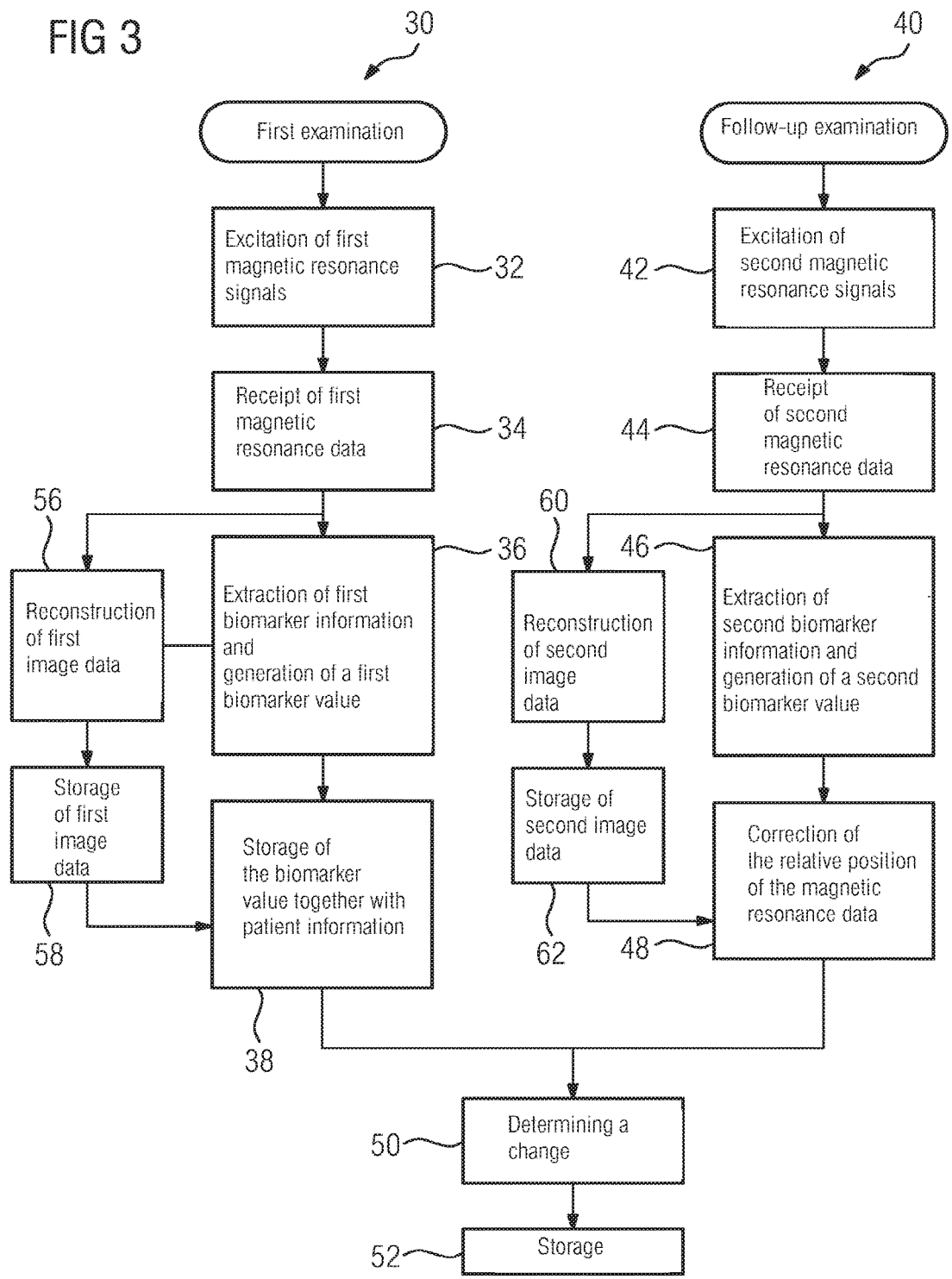

METHOD AND DEVICE FOR DETERMINING A CHANGE OVER TIME IN A BIOMARKER IN A REGION TO BE EXAMINED

CROSS REFERENCE TO RELATED APPLICATIONS

This application is a continuation application of and claims priority under 35 U.S.C. § 120/121 to U.S. application Ser. No. 13/894,623 filed May 15, 2013, which claims priority to German application No. 10 2012 209 059.2 DE filed May 30, 2012, the contents of each of which are hereby incorporated herein by reference in their entirety and for all purposes.

FIELD OF INVENTION

The present invention relates to a method and a device for determining a change over time in a biomarker in a region to be examined of a patient from magnetic resonance data.

BACKGROUND OF INVENTION

Biomarkers are characteristic biological features which can be measured objectively and can point to a normal biological or abnormal process in the body. A biomarker can be cells, genes, gene products or certain molecules such as enzymes or hormones. Complex organ functions or characteristic changes in biological structures are used as medical biomarkers. Reliable diagnosis of the disease is essential especially in the case of chronic diseases, for the treatment of which the patient potentially has to take medication, with the corresponding side effects, for a number of years. In this respect biomarkers are becoming ever more important because they can secure a difficult diagnosis or even enable it in the first place.

The treatment of psychiatric diseases such as depression, states of anxiety, manias, schizophrenia, etc. constitutes a considerable challenge. The positive effect of pharmacological active ingredients such as (selective) serotonin-re-uptake inhibitors (S)SRI), neuroleptica, etc. typically requires several weeks to improve the symptoms and months to years for healing. The dilemma arises therefrom for the patient and doctor of weighing up the sometimes severe side effects which worsen symptoms against the long-term effect of the medication. Until now the success of forms of treatment such as sport in cases of depression or anxiety states has been difficult to measure and integrate in a treatment.

Various magnetic resonance imaging methods have been evaluated in research which may be of significance to diagnostics and differential diagnostics as well as to treatment monitoring. Four magnetic resonance imaging methods are briefly presented here.

1. Resting state functional magnetic resonance imaging (resting-state fMRI or rsfMRI) determines by means of BOLD-EPI data the connectivity between individual areas of the brain which are functionally connected to each other. These different areas of the brain are called resting state networks and communicate with each other, such as, for example, the amygdala as the center of emotional processing, the thalamus as the hub for the distribution of sensory input, the hippocampus as short-term memory and learning or the prefrontal cortex for conscious planning and control. There are clear indications that the resting state fMRI method is suitable for the single diagnosis of patients, i.e. the rs-fMRI method has the stability and robustness required for a clinical application.

2. Arterial Spin Labeling (ASL) is a method of magnetic resonance imaging in which the perfusion in the human tissue is measured with an endogenous tracer—i.e. non-invasively. ASL is based on the fact that the proton spins in the blood of the arteries are magnetically marked upstream to the imaging layer. ASL is also used for example to measure a local increase in the blood perfusion in individual regions of the brain.

3. Morphometric methods in turn aim at measuring the size of different regions of the brain. Treatments such as the administering of SSRIs have the effect for example of increasing the size of the amygdala, and this, in turn, can be associated with emotional recovery.

4. Magnetic resonance spectroscopy is also used to determine conclusions about abnormal changes in individual areas of the brain.

SUMMARY OF INVENTION

The object of the present invention accordingly consists in disclosing a method and a device for carrying out the method which dovetails a treatment of patient with at least one biomarker or even a plurality of different biomarkers and thereby constitutes the basis of effective magnetic resonance-assisted treatment monitoring. In particular the change, which occurs over time during the course of the treatment, in the biomarker or biomarkers is to be robustly determined and processed by a magnetic resonance system.

The objects are achieved by the features of the claims.

The inventive method for determining a change over time in a biomarker in a region to be examined of a patient from magnetic resonance data accordingly comprises the following steps:

a) exciting first magnetic resonance signals in the region to be examined using a first magnetic resonance measuring sequence for detecting at least one property of the at least one biomarker in the region to be examined, b) receiving first magnetic resonance data from the region to be examined, wherein the first magnetic resonance data contains a first item of information relating to the at least one property, c) extracting the first item of information relating to the at least one property from the first magnetic resonance data and producing a first biomarker value from the first item of information, d) storing the first biomarker value together with an item of patient information, e) in a follow--up examination exciting second magnetic resonance signals in the region to be examined using a second magnetic resonance measuring sequence for detecting the at least one property of the at least one biomarker in the region to be examined, f) in the follow-up examination receiving second magnetic resonance data from the region to be examined, wherein the second magnetic resonance data contains a second item of information relating to the at least one property, g) in the follow-up examination extracting the second item of information relating to the at least one property from the second magnetic resonance data and producing a second biomarker value from the second item of information, h) in the follow-up examination storing the second biomarker value together with the patient information, i) determining a change between the first and second biomarker values using the patient data and j) storing or outputting the change.

The inventive device accordingly comprises a magnetic resonance device which comprises measuring sequences and protocols for measuring at least one biomarker, a control unit connected to the magnetic resonance device and which is designed to evaluate the at least one biomarker, a data memory, connected to the control unit, for storing a result of the evaluation of the biomarker, wherein during a follow-up examination the control unit is also designed to use at least one previous result from the data memory for determining a quantitative change in the at least one biomarker.

The method disclosed above and the device disclosed above prescribe for the first time a technical solution as to how a change in the biomarker, which occurs over time during the course of the treatment, can be robustly determined and processes with the aid of a magnetic resonance system.

The inventive method is basically suitable for treatment monitoring or the diagnosis of all changes in a living body which can be detected by means of magnetic resonance technology. This includes follow-ups over time of biomarkers in the case of psychiatric diseases, such as depression, anxiety states, manias, schizophrenia, etc., in the case of degenerative neurological diseases, such as Alzheimer's disease, in the case of obstructive lung diseases (COPD=chronic obstructive pulmonary disease) and asthma.

The biomarkers, which may be determined by means of magnetic resonance technology and are suitable for verifying psychiatric diseases, include by way of example what are known as functional resting state connectivity, arterial spin labeling (ASL), spectra of one or more voxel(s) and the morphometry of one of more organ(s).

In an advantageous embodiment the information stored in the database is used to carry out the follow-up examination in a simplified manner. Therefore shift scheduling for example can be omitted in that the parameters of the selected shifts in the previous examination can be used again in the follow-up examination, or only certain areas can be measured which were already identified in the first examination. Measuring time can be saved as a result. If position and volume of the amygdala for example has already been segmented and measured in the first examination, a morphological magnetic resonance examination can be restricted to this volume in the follow-up examination and does not need to measure any data relating to the remainder of the brain.

In a further embodiment the database is preferably set up such that it can be reached via the Internet so different examination centers can access the data if, for example, the follow-up examination is carried out in a different hospital.

One example from the field of psychiatric diseases should clarify the mode of operation of the invention. In a first examination a reduced connectivity strength S1 between two regions of the brain is established by means of resting state functional MRI (rsfMRI) and, moreover, the volume of the amygdala is measured at a number V1. In a follow-up examination, for example after four weeks, the magnetic resonance data is calibrated patient-specifically in a manner identical to the magnetic resonance data of the first examination. Morphological volume data for example are therefore imaged rotatorily and translationally onto each other and the functional data of individual areas of the brain similarly corrected therefore in their relative position. This achieves two advantages: firstly, exactly the same areas of the brain are compared with each other longitudinally and secondly, the changes can be expressed relative to each other, i.e. for example S1/S2 or V1/N2. Relative changes in the biomarker values individual to the patient can be robustly determined thereby.

The device advantageously also includes a unit for producing a report which describes the change over time in the biomarkers. A summary on the healing progress or the effectiveness of the treatment can be made therefore, with the medication or other information from questionnaires also being used. These statements can be stored in the database, anonymously as well, to gain further knowledge, for example for the carrying out of clinical studies. Additional data may also be stored in the database for this purpose, for example clinical scores for evaluation of the severity of the disease or for the medication.

In a further embodiment the evaluations of an expert system are supported which is trained with the aid of the information contained in the database. Correlations of biomarkers and treatment success are automatically determined and statistically evaluated for this purpose, for example by Bayesian networks or Support Vector Machines (SVM). With the aid of these models the system calculates probabilities of success for the treatment for future patients on the basis of magnetic resonance measurements.

BRIEF DESCRIPTION OF THE DRAWINGS

Further advantageous embodiments of the inventions are characterized by the dependent claims and also emerge from the following description of exemplary embodiments with the aid of three figures, in which:

FIG. 1 shows in an overview fundamental components of an embodiment of the inventive device for determining a change over time in a biomarker in a region to be examined, FIG. 2 shows the construction of a data memory for storing biomarker values and additional patient-based data, and FIG. 3 shows the fundamental method steps of an embodiment of the inventive method of a change over time in a biomarker in a region to be examined.

DETAILED DESCRIPTION OF INVENTION

FIG. 1 shows an overview of the fundamental components and their functional connections of a device for determining a change over time in a biomarker in a region to be examined. A diagnostic magnetic resonance device 2 is designed to carry out a specific magnetic resonance measuring sequence with which a property of a biomarker or even a plurality of biomarkers can be detected. Suitable magnetic resonance measuring sequences include BOLD-EPI sequences, wherein BOLD stands for "Blood Oxygen Level Dependent", Arterial Spin Labeling sequences, and also T1- or T2-weighting imaging measuring sequences as the basis for subsequent morphometric evaluations. Spatially-resolving spectroscopy measuring sequences are also suitable for detecting properties of biomarkers.

A control unit 4 is connected to the diagnostic magnetic resonance device 2. The control unit 4 is designed to evaluate at least one biomarker from the magnetic resonance signals received from the magnetic resonance device 2. As has already been mentioned in the introduction, the biomarkers which can be evaluated include the resting state connectivity, a local increase or reduction in blood perfusion, the size of a certain region, etc.

The control unit 4 is connected by a data network 6 to a data memory 8. The data network 6 allows secure transmission of the values of the biomarker, determined by the control unit 4, to the data memory 8. In addition, image data reconstructed from the magnetic resonance signals and further patient data are transmitted via the data network 6 and stored in a database in the data memory 8 together with the biomarker values.

FIG. 1 shows another magnetic resonance device 2A and another control unit 4A which are connected to the data memory 8 via the data network 6. The function of the magnetic resonance device 2A corresponds to the function of the magnetic resonance device 2 and the function of the control unit 4A corresponds to that of control unit 4. Further examination centers may be provided with additional magnetic resonance devices and a respectively associated control unit and these can all access the data memory 8 via the data network 6. The examination centers or control units 4 and 4A are preferably connected by the Internet to the data memory 8.

A fundamental function of the embodiment of the control unit 4, the additional control unit 4A, the magnetic resonance device 2 and the additional magnetic resonance device 2A shown in FIG. 1 consists in that measuring parameters, which have been used in the applied magnetic resonance measuring sequence, are passed to the data memory 8 via the data network 6 and are stored there together with the biomarker values, the patient data and image data in a data record. These measuring parameters can then be retrieved for use in a follow-up examination. A bidirectional flow of data between the magnetic resonance device 2, control unit 4 and data memory 8 is achieved therefore. Furthermore, it is also possible for measuring parameters, which were used by a first examination center in the initial examination, to be used by a second, different examination center in the follow-up examination. By way of example, measuring parameters used by the magnetic resonance device 2 are then used in the follow-up examination to control the magnetic resonance device 2A.

As already touched on briefly above, in the embodiment of the inventive device according to FIG. 1 the data memory 8 is organized as a database and comprises a large number of data fields 10. The structure of the data memory will be described below with the aid of FIG. 2.

One or more data field(s) is/are provided for storing patient data 12. This includes by way of example a patient identification number, name, age, gender, etc. The measuring parameters 16 used and a time stamp are also stored in the data memory 8 in addition to the image data 14 reconstructed from the magnetic resonance signals. Biomarker values 18 of the evaluated biomarkers are also stored in the data memory 8. Owing to the variety of biomarker values, such as volume size of an area, connectivity, perfusion, etc., this field in general also comprises a plurality of individual fields. In addition there is/are one or more data field(s) available for storing a medication 20. Further data fields are reserved for storing data collections and evaluations within the framework of clinical studies 22. Evaluation modules are connected to the data memory 8 for this purpose, and these have access to the correspondingly required data, optionally also anonymously.

Finally, there is also the possibility of outputting the data stored in the data memory 8 in the form of reports 24, optionally also in a prepared format.

FIG. 2 shows another extension of the data memory 8 with which complex evaluations of the large number of data stored in the data memory 8 are possible. An expert system 26 is therefore connected to the data memory 8, and this automatically determines and statistically evaluates correlations of biomarkers and for example treatment success. The expert system can be implemented by Bayesian networks or support vector machines. The advantage of such complex evaluations lies in particular in that models for courses of treatment can be created in a course of treatment module 28 and be continually improved on the basis of a great deal of different data. The models can be stored in the course of treatment module 28 or in the data memory 8 or even an additional data memory (not shown). With the aid of the models the course of treatment module 28 determines probabilities of success of a certain treatment for future patients on the basis of current data, which probabilities can then be retrieved via the data network 6.

FIG. 3 shows the fundamental method steps of an embodiment of the present invention. A first examination 30 of the patient begins in the magnetic resonance device 2, already described in the introduction, after the capture of fundamental patient data. The first examination 30 includes an excitation of first magnetic resonance signals 32 with a magnetic resonance measuring sequence which is designed to detect a characteristic property of a biomarker. Magnetic resonance data modulated by the characteristic property is then received in method step 34. In method step 36 the control unit 4 extracts first biomarker information which is then quantified. In method step 38 the quantified biomarker information or one or more biomarker value(s) are then stored together with patient data 14 in the data memory 8.

After a specified period of, for example, four weeks a follow-up examination 40 is carried out. For this purpose measuring parameters 16 used in the first examination 30 are retrieved from the data memory 8 and used for the follow-up examination 40. Analogously to the first examination 30 the follow-up examination 40 also includes an excitation of, in this instance, second magnetic resonance signals 42 with the magnetic resonance sequence which is designed to re-detect the characteristic property of the biomarker determined from the first examination. Second magnetic resonance data modulated by the characteristic property is then received in method step 44. In method step 46 the control unit 4 then extracts second biomarker information which is then quantified. In method step 48 the quantified second biomarker information is then stored together with patient data in the data memory 8.

A quantitative change is then determined from first and second quantified biomarker information in the control unit 4 or 4A and stored in the data memory 8 and also output by the controller 8.

Alternatively the quantitative change in the biomarker values can also be determined in a central evaluation associated with the data memory 8 but not shown here. The change is then stored in the data memory 8 and can be retrieved by an authorized examination center.

As already described with the aid of FIG. 2, additional data is stored together with the biomarker values 18 or the quantified biomarker information in the data memory 8, but this is not shown again in FIG. 3 for reasons of clarity.

The invention claimed is:

1. A method for determining a change over time in a biomarker in a region to be examined of a patient from magnetic resonance data, comprising:
   extracting a first item of information from a first magnetic resonance data of the region, the first magnetic resonance data being obtained from excitation of a first magnetic resonance signal in the region using a first magnetic resonance measuring sequence for detecting at least one property of the biomarker in the region, the first item of information relating to the at least one property;
producing a first biomarker value from the first item of information;
storing the first biomarker value in association with patient information;
extracting a second item of information from a second magnetic resonance data of the region, the second magnetic resonance data being obtained from excitation of a second magnetic resonance signal in the region using a second magnetic resonance measuring sequence for detecting the at least one property of the biomarker in the region in a follow-up examination, the second item of information relating to the at least one property;
producing a second biomarker value from the second item of information;
storing the second biomarker value in association with the patient information;
determining a change between the first and the second biomarker values; and
storing or outputting the change between the first and the second biomarker values,
wherein the biomarker includes at least one of,
a correlation between individual areas of a brain of the patient,
a perfusion behavior in the brain, and
a morphology of an area of the brain, with the at least one property being a size of an area of the brain.

2. The method as claimed in claim 1, wherein first and second image data are respectively reconstructed from the first and the second magnetic resonance data, and the first and the second image data are stored together in association with the first and the second biomarker value, respectively.

3. The method as claimed in claim 1, wherein parameters of the first magnetic resonance measuring sequence are stored in association with the first biomarker value and the patient information, and the parameters are used during the second magnetic resonance measuring sequence.

4. The method as claimed in claim 1, wherein the extracted first item of information is stored in association with the first biomarker value, and the first item of information is used during the second magnetic resonance measuring sequence.

5. The method as claimed in claim 1, wherein the storing the first biomarker value, the storing the second biomarker value, the storing or outputting the change between the first and the second biomarker values, a sub-combination thereof or a combination thereof occurs on a central data memory via a data network.

6. The method as claimed in claim 5, wherein the data network is Internet.

7. The method as claimed in claim 1, wherein the biomarker is the correlation between individual areas of the brain and the first and second magnetic resonance measuring sequences are resting state magnetic resonance sequences.

8. The method as claimed in claim 1, wherein the biomarker is the perfusion behavior of the brain and the first and second magnetic resonance measuring sequences are Arterial Spin Labeling sequences.

9. The method as claimed in claim 1, wherein the biomarker is the morphology of the area of the brain.

10. The method as claimed in claim 1, wherein the first and the second magnetic resonance data are calibrated with each other before extracting the second item of information.

11. The method as claimed in claim 1, wherein the first and the second magnetic resonance data are imaged rotationally and translationally onto each other.

12. The method as claimed in claim 1, further comprising:
retrieving further patient information with the change between the first and the second biomarker values from a memory.

13. The method as claimed in claim 12, wherein a system is connected to the memory and is trained by at least one of (i) data stored in the memory and (ii) evaluations in a correlation of the biomarker and a treatment.

14. A device for determining a quantitative change over time in a biomarker in a region to be examined of a patient from magnetic resonance data, comprising:
a control unit configured to receive the magnetic resonance data from a magnetic resonance device, the control unit configured to evaluate the biomarker from the magnetic resonance data; and
a data memory connected to the control unit for storing results of the evaluation,
wherein the control unit is configured to use at least one previous result of the evaluation from the data memory to determine the quantitative change in the biomarker during a follow-up examination, and
wherein the biomarker includes at least one of,
a correlation between individual areas of a brain of the patient,
a perfusion behavior in the brain, and
a morphology of an area of the brain, with at least one property of the biomarker being a size of the area of the brain.

15. The device as claimed in claim 14, wherein the control unit is configured to use at least one previous item of image information from the data memory to determine the quantitative change in the biomarker during the follow-up examination.

16. A method for determining a change over time in a biomarker in a region to be examined of a patient from magnetic resonance data, comprising:
extracting a first item of information from a first magnetic resonance data of the region, the first magnetic resonance data being obtained from excitation of a first magnetic resonance signal in the region using a first magnetic resonance measuring sequence for detecting at least one property of the biomarker in the region, the first item of information relating to the at least one property;
producing a first biomarker value from the first item of information;
storing the first biomarker value in association with patient information;
extracting a second item of information from a second magnetic resonance data of the region, the second magnetic resonance data being obtained from excitation of a second magnetic resonance signal in the region using a second magnetic resonance measuring sequence for detecting the at least one property of the biomarker in the region in a follow-up examination, the second item of information relating to the at least one property;
producing a second biomarker value from the second item of information;
storing the second biomarker value in association with the patient information;
determining a change between the first and the second biomarker values; and storing or outputting the change between the first and the second biomarker values, wherein the first and the second magnetic resonance data are imaged rotationally and translationally onto each other.

17. The method as claimed in claim 16, wherein first and second image data are respectively reconstructed from the first and the second magnetic resonance data, and the first and the second image data are stored together in association with the first and the second biomarker value, respectively.

18. The method as claimed in claim 16, wherein parameters of the first magnetic resonance measuring sequence are stored in association with the first biomarker value and the patient information, and the parameters are used during the second magnetic resonance measuring sequence.

19. The method as claimed in claim 16, wherein the extracted first item of information is stored in association with the first biomarker value, and the first item of information is used during the second magnetic resonance measuring sequence.

20. The method as claimed in claim 16, wherein the storing the first biomarker value, the storing the second biomarker value, the storing or outputting the change between the first and the second biomarker values, a subcombination thereof or a combination thereof occurs on a central data memory via a data network.

21. The method as claimed in claim 20, wherein the data network is Internet.

22. The method as claimed in claim 16, wherein the biomarker is a correlation between individual areas of a brain and the first and second magnetic resonance measuring sequences are resting state magnetic resonance sequences.

23. The method as claimed in claim 16, wherein the biomarker is a perfusion behavior in a brain and the first and second magnetic resonance measuring sequences are Arterial Spin Labeling sequences.

24. The method as claimed in claim 16, wherein the biomarker is a morphology of an area of a brain.

25. The method as claimed in claim 16, wherein the first and the second magnetic resonance data are calibrated with each other before the extracting the second item of information.

26. The method as claimed in claim 16, wherein further comprising:

retrieving further patient information with the change from a memory.

27. The method as claimed in claim 26, wherein a system is connected to the memory and is trained by at least one of (i) data stored in the memory and (ii) evaluations in a correlation of the biomarker and a treatment.

28. A device for determining a quantitative change over time in a biomarker in a region to be examined of a patient from magnetic resonance data, comprising:

a control unit connected to a magnetic resonance device, the control unit configured to receive first magnetic resonance data of the patient in a first examination from the magnetic resonance device, receive a second magnetic resonance data of the patient from the magnetic resonance device in a follow-up examination, and evaluate the biomarker based on at least one the first magnetic resonance data and the second magnetic resonance data; and a data memory connected to the control unit for storing results of the evaluation, wherein the control unit is configured to use at least one previous result of the evaluation from the data memory to determine the quantitative change in the biomarker from the follow-up examination, and wherein the first and the second magnetic resonance data are imaged rotationally and translationally onto each other.

29. The device as claimed in claim 28, wherein the control unit is configured to use at least one previous item of image information from the data memory to determine the quantitative change in the biomarker during the follow-up examination.

30. The device as claimed in claim 28, wherein the biomarker is selected from the group consisting of:

a correlation between individual areas of a brain of the patient, with a magnetic resonance measuring sequence being a resting state magnetic resonance sequence, a perfusion behavior in the brain, with the magnetic resonance measuring sequence being an Arterial Spin Labeling sequence, and a morphology of an area of the brain, with at least one property of the biomarker being a size of the area of the brain of the patient.

31. A non-transitory computer-readable medium, when executed by at least one control unit, configured to cause the at least one control unit to evaluate a biomarker in a region of a patient; and use at least one previous result of an evaluation of the biomarker to determine a quantitative change in the biomarker during a follow-up examination, wherein the biomarker includes at least one of, a correlation between individual areas of a brain of the patient, with magnetic resonance measuring sequences for evaluating the biomarker being resting state magnetic resonance sequences, a perfusion behavior in the brain, with the magnetic resonance measuring sequences being Arterial Spin Labeling sequences, and a morphology of an area of the brain, with at least one property of the biomarker being a size of the area of the brain.

* * * * *

UNITED STATES PATENT AND TRADEMARK OFFICE
CERTIFICATE OF CORRECTION

| | |
|---|---|
| PATENT NO. | : 10,365,342 B2 |
| APPLICATION NO. | : 15/467427 |
| DATED | : July 30, 2019 |
| INVENTOR(S) | : Bjoern Heismann, Arne Hengerer and Sebastian Schmidt |

Page 1 of 1

It is certified that error appears in the above-identified patent and that said Letters Patent is hereby corrected as shown below:

On the Title Page

Item (30) Foreign Application Priority Data should read as follows:
May 30, 2012 (DE) ............ 10 2012 209 059

Signed and Sealed this
Twenty-eighth Day of April, 2020

Andrei Iancu
*Director of the United States Patent and Trademark Office*